(12) United States Patent
Lollar et al.

(10) Patent No.: US 6,517,830 B1
(45) Date of Patent: Feb. 11, 2003

(54) COMPOSITIONS AND METHODS FOR THE EXPRESSION OF FACTOR VIII POLYPEPTIDES AND USES THEREFOR

(75) Inventors: John S. Lollar, Decatur, GA (US); Hung V. Do, Atlanta, GA (US); John F. Healey, Snellville, GA (US); Edmund K. Waller, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/633,020

(22) Filed: Aug. 4, 2000

Related U.S. Application Data
(60) Provisional application No. 60/147,407, filed on Aug. 5, 1999.

(51) Int. Cl.$^7$ .......................... A01N 63/00; A61K 48/00
(52) U.S. Cl. ..................... 424/93.21; 514/44; 435/320.1
(58) Field of Search ........................ 514/44; 435/720.1; 424/93.21

(56) References Cited

U.S. PATENT DOCUMENTS

| | | | |
|---|---|---|---|
| 4,868,112 A | * 9/1989 | Toole, Jr. ..................... | 435/68 |
| 5,681,746 A | 10/1997 | Bodner | |
| 5,744,446 A | 4/1998 | Lollar | |
| 6,087,129 A | 7/2000 | Newgard | |

OTHER PUBLICATIONS

Riddell et al., T–cell mediated rejection of gene–modified HIV–specific cytotoxic T lymphocytes in HIV–infected patients, 1996, Nature Medicine, vol. 2, pp. 216–223.*

Cid–Arregui et al., Viral Vectors: Basic science and gene therapy, 2000, Biotechniques Books, pp. 223.*

Chiu et al., Optimizing energy potentials for success in protein tertiary structure prediction, 1998, Folding & Design, vol. 3, pp. 223–228.*

Hegenbarth et al., Liver sinusoidal endothelial cells are not permissive for adenovirus 2000, Human Gene Therapy, vol. 11, pp. 481–486.*

Walter et al., Gene therapy for the hemophilas 1997, Advances in Veterinary Medicine, vol. 40, pp. 119–134.*

Freiburghaus et al., Tolerance induction using the Malmo treatment model 1982–1995, 1999, Haemophilia, vol. 5, pp. 32–39.*

Connelly et al. (1996) "High–Level Tissue–Specific Expression of Functional Human Factor VIII in Mice" *Human Gene Therapy* 7:183–195.

Connelly et al. (1998) "Sustained Phenotypic Correction of Murine Hemophilia A by In Vivo Gene Therapy" *Blood* 91(9):3273–3281.

Do et al. (1999) "Expression of Factor VIII by Murine Liver Sinusoidal Endothelial Cells" *J. Biol. Chem.* 274(28):19587–19592.

Hellman et al. (1989) "Secretion of Coagulant Factor VIII Activity and Antigen by In Vitro Cultivated Rat Liver Sinusoidal Endothelial Cells" *British J. Haematology* 73:348–355.

(List continued on next page.)

*Primary Examiner*—Dave T. Nguyen
*Assistant Examiner*—Brian Whiteman
(74) *Attorney, Agent, or Firm*—Alston & Bird LLP

(57) ABSTRACT

Compositions and methods are provided for the in vivo gene delivery of nucleic acid sequences encoding the factor VIII protein to the liver endothelial sinusoidal cells (LSECs). Compositions and methods are also provided for the ex vivo gene transfer of nucleic acid sequences encoding the factor VIII protein to cultured LSECs and the implantation of the transformed LSECs in vivo. These methods and compositions increase the level of factor VIII in the blood stream and find use in the gene therapy treatment of hemophilia A.

12 Claims, 2 Drawing Sheets

OTHER PUBLICATIONS

Herzog et al. (1998) "Problems and Prospects in Gene Therapy for Hemophilia" *Current Opinion in Hematology* 5(5):321–326.

Ill et al. (1997) "Optimization of the Human Factor VIII Complementary DNA Expression Plasmid for Gene Therapy of Hemophilia A" *Blood Coagulation and Fibrinolysis* 8(*Suppl 2*):S23–S30.

Kadhom et al. (1988) "Factor VIII Procoagulant Antigen in Human Tissues" *Thrombosis and Haemostasis* 59(2):289–294.

Kwast et al. (1986) "Localization of Factor VIII–Procoagulant Antigen: An Immunohistological Survey of the Human Body Using Monoclonal Antibodies" *Blood* 67(*1*):222–227.

Lenting et al. (1998) "The Life Cycle of Coagulation Factor VIII in View of Its Structure and Function" *Blood* 92(*11*):3983–3996.

Shima et al. (1988) "Factor VIII Polypeptide Specificity of Monoclonal Anti–factor VIII Antibodies" *British J. Haematology 70*:63–69.

Stel et al. (1983) "Detection of Factor VIII/Coagulant Antigen in Human Liver Tissue" *Nature 303*:530–532.

Van Der Eb et al. (1996) "Liver–Directed Gene Therapy for Factor–VIII Deficiency" *J. Clinical Biochemistry and Nutrition*21(l):78–80.

Wion et al. (1985) "Distribution of Factor VIII mRNA and Antigen in Human Liver and Other Tissues" *Nature 317*:726–729.

Zelechowska et al. (1985) "Ultrastructural Localization of Factory VIII Procoagulant Antigen in Human Liver Hepatocytes" *Nature 317*:729–730.

* cited by examiner

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 1
gcccatgctg agaagatacc atcg                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
gtattgctgc tgggcctcac atcc                                          24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
ttttccccag ccactgacat agcca                                         25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
ggcagttgca gaccctcctt g                                             21

<210> SEQ ID NO 5
```

```
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
gtccctactc cttctattct agcc                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
gcccatgctg agaagatacc atcg                                          24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 7
cttcgcatgg agttgatggg ctgt                                          24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
tcatcatagg tgtggatgag tcctg                                         25

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
ctcgagttgt tggtggagaa aacg                                          24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
ttttccccag ccactgacat agcca                                         25

<210> SEQ ID NO 11
<211> LENGTH: 21
```

```
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
atgatggaga ggttacacat c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
ggcagttgca gaccctcctt g                                              21

<210> SEQ ID NO 13
<211> LENGTH: 67
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
aaaactgcag gtccctactc cttctattct agccgtcaag cctaatgaaa ccaaaattta   60
tttttgg                                                              67

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
ttttctgcag gcccatgctg agaagatacc atcg                                34

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
aaaactgcag cttcgcatgg agttgatggg ctgtagatac acaaatcact gcctcatcc    59

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16
ttttctgcag gtattgctgc tgggcctcac atcctag                             37
```

COMPOSITIONS AND METHODS FOR THE EXPRESSION OF FACTOR VIII POLYPEPTIDES AND USES THEREFOR

CROSS-REFERENCE TO RELATED APPLICATIONS

This application claims the benefit of U.S. Provisional Application Ser. No. 60/147,407, filed Aug. 5, 1999, the contents of which are herein incorporated by reference.

FIELD OF THE INVENTION

The invention relates to methods for the expression and secretion of factor VIII polypeptides.

BACKGROUND OF THE INVENTION

Hemophilia A affects one in every 10,000 males and is caused by a deficiency of the factor VIII protein in the plasma. Based on the level of factor VIII activity in the blood, hemophilia A is categorized into mild, moderate, and severe forms. Fifty percent of hemophilia A patients have the severe form of the disease that is characterized by spontaneous and prolonged bleeding episodes.

Factor VIII is a cofactor in the coagulation pathway. Circulating in the blood, factor VIII is non-covalently complexed with its carrier protein von Willebrand factor. This interaction stabilizes factor VIII and prevents the association of factor VIII with membrane surfaces. The conversion of factor VIII into its active state, factor VIIIa, occurs via the proteolysis of factor VIII by thrombin or factor Xa. The proteolysed factor VIIIa dissociates from von Willebrand factor. A membrane bound complex containing factor VIIIa and factor IXa is formed that subsequently activates factor X in the coagulation cascade.

Currently, hemophilia A is treated by the frequent infusion of purified factor VIII into the blood. While this method of treating hemophilia A does reduce the frequency and severity of bleeding, this therapy is limited by the availability and the cost of purified factor VIII, the short half life of factor VIII in vivo, and the necessity of removing contaminating AIDS and hepatitis viruses. While, recombinant factor VIII is now available, this form of factor VIII maintenance therapy is both expensive and chronic.

Gene therapy is an attractive alternative to the protein infusion treatments for hemophilia A. Two gene therapy approaches may be used. In vivo gene therapy introduces nucleotides encoding the factor VIII protein into the patient's cells. Ex vivo gene therapy techniques introduce the nucleotides encoding the factor VIII protein into in vitro cultured cells. The transformed cultured cells are subsequently reimplanted into the patient.

Studies of factor VIII biogenesis and secretion have been limited by the lack of human cell lines that express significant amounts of factor VIII. Analysis of secretion has been limited to autologous gene expression. In general, these studies show factor VIII has low expression levels due to unstable RNA and poor secretion. See, for example, Lenting et al. (1998) Blood 92:3983–3996, Connelly et al. (1996) Human Gene Therapy 7:183–195, Kaufman et al. (1989) Mol. Cell. Biol. 9: 1233, Dorner et al. (1987) J. Cell Biol. 105:2665 and the references cited therein. These studies suggest that expression of factor VIII and secretion of factor VIII may be more efficient in cells where it is endogenously expressed.

Factor VIII mRNA is expressed in many tissues including the kidney, spleen, liver, and lymph nodes. Human and canine studies have shown that factor VIII levels rise to normal following liver transplantation, during which there can be no extrahepatic synthesis of factor VIII. This indicates that the liver synthesizes a clinically significant amount of factor VIII protein. It is well known in the art that hepatocytes express factor VIII, however, whether other types of liver cells synthesize factor VIII remains controversial. See, for reviews, Bloom et al. (1979) Clin. Haematol. 8:53–77 and Lenting (1998) Blood 92:3983–3996, both of which are herein incorporated by reference.

Many different gene therapy approaches to treat hemophilia A are currently being studied. Ex vivo gene therapy techniques have found that factor VIII protein expression is low in transformed in vitro cultured cells and undetectable in vivo (Lynch et al. (1993) Hum. Gene Therapy 4:259; Chuah et al. (1995) Hum. Gene Ther. 6:1363; Hoeben et al. (1990) J. Biol. Chem. 265:7318; Hoeben et al. (1993) Hum. Gene Ther. 4:179; Israel et al. (1990) Blood 75:1074 and van der Eb (1996) J. Clin. Biochem. Nutr. 21: 78–80; all of which are herein incorporated by reference).

Both the canine and murine systems are being used to develop in vivo therapy treatment for hemophilia A. Many of these have directed the expression of factor VIII to the liver hepatocytes (Connelly et al. (1998) Blood 91:3273–3281, Connelly et al. (1996) Human Gene Therapy 7:183–195, Connelly et al. (1996) Blood 88:3846, Giles et al. (1982) Blood 60:727). Phenotypic correction of murine hemophilia A was sustained for over 9 months through the in vivo transformation of hepatocytes. However, sustained expression was not uniformly achieved. Instead, factor VIII levels rapidly declined in certain animals over time. Yet, the level of factor VIII mRNA declined only minimally in these animals. Further characterization showed that neither the humoral immune response nor the cell-mediated immune response was responsible for the decline of factor VIII levels in the plasma. Therefore, the level of mRNA in the transformed hepatocytes did not parallel the concentration of factor VIII protein in the plasma (Connelly et al. (1998) Blood 91:3273–3281; all of which are herein incorporated by reference).

The present invention provides an improved method of factor VIII expression by targeting expression of factor VIII to cells that express a key regulatory protein involved in factor VIII biogenesis.

SUMMARY OF THE INVENTION

Compositions and methods for the expression of a nucleotide sequence encoding a factor VIII polypeptide or a functional variant thereof are provided. Specifically, the methods of the invention provide for the stable introduction of a nucleotide sequence encoding factor VIII or a functional variant thereof into an isolated LSEC. The genetically modified LSEC is subsequently cultured under conditions that allow for the expression and secretion of the factor VIII polypeptide. In one embodiment of the present invention, the culturing of the genetically modified LSECs occurs in vitro, while in other embodiments, the culturing of the genetically modified LSECs occurs in vivo.

The present invention further provides methods to increase the level of a factor VIII polypeptide or functional variant thereof in the blood stream of a subject. The method comprises the stable introduction of a nucleic acid sequence encoding the factor VIII polypeptide or a functional variant thereof into an isolated LSEC. The genetically modified LSEC is implanted into a subject such that an increased level of factor VIII polypeptide in the blood of the subject occurs.

In certain embodiments, the subject is characterized by having factor VIII deficient plasma. In other embodiments, the subject has hemophilia A.

The present invention further provides method to increase the level of a factor VIII polypeptide or a functional variant thereof in the blood stream of a subject through the stable introduction of a nucleic acid sequence encoding the factor VIII polypeptide or a functional variant thereof into an LSEC cultured in vivo. In this method the factor VIII polypeptide is preferentially produced in the LSECs, such that the levels of the factor VIII polypeptide is increased in the blood stream of the subject. In certain embodiments the subject is characterized by having factor VIII deficient plasma. In other embodiments the subject has hemophilia A.

Compositions are also provided for an isolated LSEC having stably incorporated a DNA construct comprising a nucleotide sequence encoding a factor VIII polypeptide or a function variant thereof, operably linked to a promoter active in the LSEC.

DETAILED DESCRIPTION OF THE INVENTION

Figure 1A:
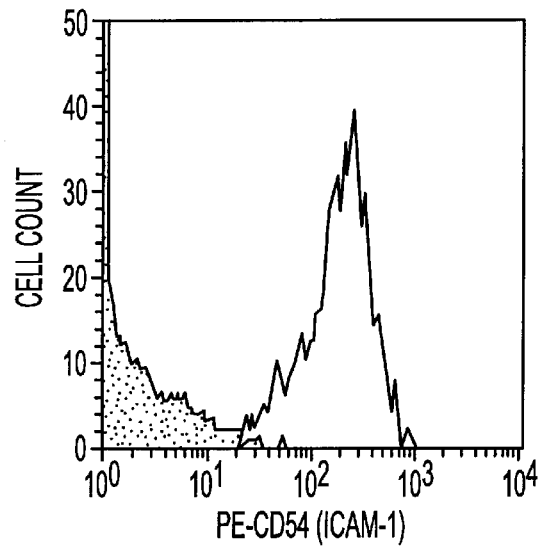
FIG. 1: Analysis of purified LSECs by flow cytometry. Staining of LSECs using fluorophore-conjugated antibodies specific for ICAM-1 (CD54) (A) and PECAM-1 (CD31) (B). The isotype control is represented by the black profile for each histogram plot. (C) Staining of LSECs with FITC-conjugated wheat germ agglutinin.

Compositions and methods are based on the unexpected result that liver sinusoidal endothelial cells (LSECs) express factor VIII. A thorough description of the compositions and methods of the present invention to treat hemophilia A through the genetic alteration of LSECs is provided below.

LSECs are referred to herein as a population of mammalian liver cells of endothelial origins that have the following phenotypic characteristics. LSECs express cell surface markers that include ICAM-1 and PECAM-1 and do not express the monocyte/macrophage specific marker CD14. The endothelial cell marker, VCAM-1, may or may not be expressed on the surface of the LSECs. Furthermore, the LSECs can be categorized into two subpopulations that differentially bind wheat germ agglutinin. Further phenotypic characteristics of LSECs include their relatively small size (8–10 um), clear cytoplasm and oval nuclei.

LSECs cultured in vitro are characterized by a spindle-shape and display long cytoplasmic extensions prior to confluence. When they approach confluence they form a polygonal, flat "cobblestone monolayer" characteristic of cultured endothelial cells. Cell surface markers expressed by cultured LSECs include ICAM-1, PCAM-1, and VCAM-1. In addition, cultured LSECs are also characterized by the ability to bind wheat germ agglutinin. The LSECs of the present invention can be obtained from any organism, preferably a vertebrate, more preferably a mammal (i.e., human, mouse, rat or pig).

The expression of factor VIII in LSECs has been controversial. Wion et al. failed to detect factor VIII mRNA in LSECs ((1985) *Nature* 317:726–729). Several other studies have localized factor VIII protein to LSECs using either immunohistochemical or electron microscopy techniques (Shimo et al. (1998) *British Journal of Hematology* 70:63–69; Kadhom et al. (1988) *Thrombosis and Haemostasis* 59:289–294; Hellman et al. (1989) *Br. J. Haematol.* 73:348–355; Theo et al. (1986) *Blood* 67:222–227; Zelechowska et al. (1985) *Nature* 317:729–730; all of which are herein incorporated by reference). These studies, however, were unable to conclude that de novo factor VIII protein synthesis is occurring in the LSECs. The localization of factor VIII protein to the LSECs may reflect the binding of factor VIII to the surface of the liver sinusoidal cells or the endocytosis of factor VIII protein into the liver sinusoidal cells.

The present invention directs the expression of factor VIII mRNA in LSECs. Von Willebrand factor plays an important role in factor VIII biogenesis. Von Willebrand factor is expressed in endothelial cells, including LSECs, and stabilizes factor VIII in the blood through a non-covalent interaction. In addition, considerable evidence exists that von Willebrand factor increases secretion of stored factor VIII. See, for example, Bloom (1979) *Clin. Haematol.* 8:53–73; Lenting et al. (1998) *Blood* 92:3983–3996, Cornu et al. (1963) *Br. J. Haematol.* 9:189, Weiss (1977) *J. Clin. Invest.* 60:390–404, Kaufman et al. (1999) *Blood* 93:193–197, all of which are herein incorporated by reference. Therefore, the expression of both factor VIII and von Willebrand factor in the LSECs raises the possibility of coordinate gene regulation in vivo. The genetic alteration of LSECs to express factor VIII offers an improved gene therapy treatment of hemophilia A. Factor VIII will be expressed under physiological conditions, particularly with respect to the regulatory control by von Willebrand factor.

Hence, the methods of the present invention provide for the treatment of hemophilia A or a factor VIII deficiency through the use of LSEC cells that have been genetically modified to express a factor VIII polypeptide or a functional variant thereof. Therapy via this method, i.e. with the genetically modified LSECs, involves the genetic manipulation of LSECs either in vivo or ex vivo to induce them to express and secrete the factor VIII polypeptide or functional variant thereof. In the ex vivo approach, the LSECs are modified in vitro, followed by implantation of the cells into the patient, as generally described in Seldon et al. WO 93/09222, herein incorporated by reference. Alternatively, the methods of the invention provide for the treatment of hemophilia A using purified factor VIII polypeptide obtained from cultured, genetically altered LSEC cells.

The present invention preferentially directs the expression of factor VIII in LSECs and thereby finds use in increasing the levels of factor VIII circulating in the blood stream. The phrase "increase" is used herein to mean an elevation of factor VIII mRNA expression and protein synthesis in the transformed LSECs. In addition, the phrase "increase" is also used to mean an elevation of factor VIII protein secreted from the LSEC. In specific embodiments of the present invention, the transformed LSEC is cultured in vitro. In this embodiment, the increased secretion of the factor VIII polypeptide elevates the activity of factor VIII in the cell culture supernate. In other embodiments of the present invention, the transformed LSEC is cultured in vivo. In this embodiment, the increased secretion of the factor VIII polypeptide elevates the level of factor VIII in the bloodstream as compared to the levels of factor VIII found in the bloodstream prior to the genetic alterations of the LSECs.

As used herein, "preferential expression" in LSECs is used to indicate that approximately about 20% to about 30%, about 30% to about 50%, about 50% to 60%, about 60% to about 70%, about 70% to 80%, 80% to 90%, or 90% or greater of the overall increase in factor VIII protein levels in the blood is attributed to an increase in factor VIII mRNA expression in LSECs.

A "transformed" LSEC has been genetically altered to express the factor VIII protein through the stable introduction of a DNA molecule encoding factor VIII or a functional variant thereof. The factor VIII protein secreted into the blood from the transformed LSECs will have biological activity, defined herein as the ability to correct the coagulation defect of factor VIII deficient plasma. Factor VIII activity is assayed by measuring the clotting time of human factor VIII deficient plasma compared to normal human plasma. A "factor VIII deficiency" includes a deficiency in clotting activity caused by production of defective factor VIII, by altered levels of factor VIII expression, or by partial or total inhibition of factor VIII by inhibitors. A type of factor VIII deficiency is hemophilia A. One unit of factor VIII activity is defined as the coagulation activity in 1 ml of normal human plasma.

The increase of factor VIII in the plasma will be sufficient to produce a therapeutic effect. A "therapeutic effect" is defined as an increase in the blood coagulation activity in the plasma of patients that is greater than the coagulation activity observed in the subject before the genetic alteration of the LSECs. In a standard blood clotting assay, the shorter time for clot formation, the greater the activity of factor VIII being assayed. An increase in factor VIII activity in the factor VIII deficient plasma of at least 1% or higher will be therapeutically beneficial.

The nucleotide sequence encoding the factor VIII polypeptide used in the methods of the present invention may be obtained from any mammal, including both human and non-human mammals (such as pig, rat and mouse). Such sequences are known in the art. See, for example, U.S. Pat. Nos. 4,965,199 and 4,744,446 and Wood et al. (1984) *Nature* 312:330.

Biologically active variants of factor VIII are also encompassed by the methods of the present invention. Such variants should retain factor VIII activities, particularly the ability to correct the coagulation defect of factor VIII deficient plasma. Factor VIII activity may be measured using standard coagulation assays or a plasma-free tenase assay using purified proteins. See, for example, U.S. Pat. No. 5,681,746 herein incorporated by reference. Preferably, the variant has at least the same activity as the native molecule.

Suitable biologically active variants can be factor VIII fragments, analogues, and variants. By "factor VIII fragment" is intended a protein consisting of only a part of the intact factor VIII sequence and structure, and can be a C-terminal deletion or N-terminal deletion of factor VIII. By "analogues" is intended analogues of either factor VIII or a factor VIII fragment that comprise a native factor VIII sequence and structure having one or more amino acid substitutions, insertions, or deletions. Peptides having one or more peptoids (peptide mimics) are also encompassed by the term analogue (see International Publication No. WO 91/04282). By "variant" is intended any suitable modification of factor VIII, factor VIII fragments, or their respective analogues, such as glycosylation, phosphorylation, or other addition of foreign moieties, so long as the factor VIII activity is retained (i.e., the ability to correct the coagulation defect of factor VIII deficient plasma). Representative examples of variants include addition, deletion, or movement of one or more sulfation sites, glycosylation sites, etc. Also, changes may be engineered to improve metal binding, ion binding or thrombin interactions. See, for example, Pittman et al. (1992) *Biochem* 31:3315, U.S. Pat. No. 5,744,446, both of which are herein incorporated by reference.

Factor VIII variants will generally have at least 70%, preferably at least 80%, more preferably about 90%, 91%, 92%, 93%, 94%, 95%, 96%, 97%, 98%, 99% more amino acid sequence identity to the amino acid sequence of the reference factor VIII molecule. The sequence for factor VIII is known in the art. See, for example, U.S. Pat. Nos. 4,965,199 and 4,744,446, both of which are herein incorporated by reference. A variant may differ by as few as 1–15 amino acids, as few as 1–10, such as 6–10, as few as 5, as few as 4, 3, 2, or even 1 amino acid residue. By "sequence identity" is intended the same amino acid residues are found within the factor VIII variant and the reference factor VIII molecule when a specified, contiguous segment of the amino acid sequence of the variant is aligned and compared to the amino acid sequence of the reference molecule.

For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous nucleotides, and may be 30, 40, 50, 100, or more nucleotides. Corrections for increased sequence identity associated with inclusion of gaps in the variant's amino acid sequence can be made by assigning gap penalties. Methods of sequence alignment are well known in the art.

The determination of percent identity between two sequences can be accomplished using a mathematical algorithm. A preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. A PAM120 weight residue table, a gap length penalty of 12, and a gap penalty of 4 can be used when utilizing the ALIGN program for comparing amino acid sequences. An additional preferred program is the Pairwise Alignment Program (Sequence Explorer), using default parameters. Another nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. Nucleotide sequences homologous to the factor VIII nucleic acid molecules of the invention can be obtained using BLAST nucleotide searches performed with the NBLAST program, score=100, wordlength=12. BLAST protein searches can be performed with the XBLAST program, score=50, wordlength=3, to obtain amino acid sequences homologous to factor VIII protein molecules of the invention. To obtain gapped alignments for comparison purposes, Gapped BLAST can be utilized as described in Altschul et al. (1997) *Nucleic Acids Res.* 25:3389. Alternatively, an iterated search that detects distant relationships between molecules can be performed using PSI-Blast. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Such adjustments are well known in the art. See, for example, Meyers and Miller (1988) *Computer Applic. Biol. Sci.* 4:11–17. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

The art provides substantial guidance regarding the preparation and use of such factor VIII variants, as discussed further below. A fragment of factor VIII will generally include at least about 10 contiguous amino acid residues of the full-length molecule, preferably about 15–25 contiguous amino acid residues of the full-length molecule, and most preferably about 20–50 or more contiguous amino acid residues of full-length factor VIII. In preparing the factor VIII variants, one of skill in the art can readily determine which modifications to the native protein nucleotide or amino acid sequence will result in a variant of factor VIII in accordance with the methods disclosed in the present invention. Such variant sequences include, for example, any modifications made to the nucleic acid sequence of factor VIII that improve the secretion of factor VIII from the LSECs, increase expression levels, or decrease the immunogenicity of the expressed factor VIII protein. See, for example, Yang et al. (1996) *Gene Ther* 3:137–144; Connelly et al. (1996) *Human Gene Therapy* 7:183–195; herein incorporated by references.

Fragments and variants of the factor VIII protein used in the present invention further include a hybrid factor VIII polypeptide. By "hybrid polypeptide" is intended the fusion of two or more nucleotide sequences encoding a polypeptide, such that expression of the hybrid sequence results in the in frame fusion between the two amino acid sequences. Examples of such hybrid factor VIII polypeptides can be found in, for example, U.S. Pat. No. 5,744,446, herein incorporated by reference.

To direct the expression of factor VIII protein or a variant in the LSECs, a nucleic acid sequence encoding a factor VIII polypeptide or a functional variant thereof is placed in an expression cassette. The nucleic acid sequence encoding factor VIII may contain genomic or complementary DNA.

In the methods of the present invention, a nucleotide sequence encoding a factor VIII polypeptide or functional variant thereof is contained in an expression cassette designed to optimize expression of the factor VIII polypeptide in LSECs. The expression cassette can include a variety of enhancers/promoters from both viral and mammalian sources that drive expression in LSECs. The expression cassette can further contain 3' regulatory sequences and nucleic acid sequences that facilitate subcloning and recovery of the DNA. Furthermore, selectable markers are well known in the art and can be used to establish permanent stable LSEC clones expressing factor VIII polypeptide.

The transcriptional promoter and, if desired, the transcriptional enhancer element are operably linked to the nucleic acid sequence of the factor VIII protein. A "promoter" is defined as a minimal DNA sequence that is sufficient to direct transcription of a nucleic acid sequence. A "transcriptional enhancer element" refers to a regulatory DNA sequence that stimulates the transcription of the adjacent gene. The nucleic acid sequence encoding the factor VIII polypeptide is operably linked to the promoter sequence. "Operably linked" is used herein to refer to a functional linkage between the regulatory promoter and the nucleic acid sequence of the factor VIII polypeptide. The functional linkage permits gene expression of factor VIII when the appropriate transcription activator proteins are present.

The expression cassette will include a promoter that may be native or foreign. By "foreign" it is meant a sequence not found in the native organism. Furthermore, the transcription regulatory elements may be heterologous to the nucleotide sequence encoding factor VIII. By "heterologous" is intended any nucleotide sequence not naturally found upstream of the sequence encoding the factor VIII polypeptide. The promoter may be a natural sequence or a synthetic sequence. In addition, the promoter may be constitutively active or tissue-specific. A tissue-specific promoter is preferentially activated in a given tissue and results in expression of a gene product in the tissue where activated. In particular endothelial-specific promoters or more specifically, LSEC-specific promoters can be used. Endothelial-specific promoters include, but are not limited to, regulatory regions of von Willebrand factor (Jahroudi, N. et al. (1994) *Molecular and Cellular Biology* 14:999–1008), intercellular adhesion molecule 2 (ICAM-2) (Cowan, P. J. et al. (1998) *J. Biol. Chem.* 273:11737–11744), vascular endothelial-cadherin (Gory, S. et al. (1999) *Blood* 93:184–192), endothelial nitric oxide synthase (Guillot, P. V. et al. (1999) *J. Clin. Invest.* 103:799–805), Tie (an endothelial cell-specific receptor tyrosine kinase) (Iljin, K. et al.(1999) *FASEB* 13:377–386), endoglin (Rius, C. et al. (1998) *Blood* 92:4677–4690), and thrombomodulin (Tazawa R. et al. (1993) *Journal of Biochemistry* 113:600–606).

Examples of liver-specific promoters include but are not limited to the albumin promoter (Hafenrichter et al. (1994) *Blood* 10:3394–3404, Pinkert et al. (1987) *Genes and Devel.* 1:268–276); the alpha-fetoprotein promoter (Krumlauf et al. (1985) *Mol. Cell. Biol.* 5:1639–1648; Hammer et al. (1987) *Science* 235:53–58); the alpha-1-antitrypsin promoter (Kelsey et al. (1987) *Genes and Devel.* 1:161–171), and the thyroid-binding globulin promoter (Hayashi, Y. et al. (1993) *Mol. Endocrinol.* 7:1049–1060).

An LSEC-specific promoter may also be used to ensure preferential expression of VIII in the LSECs. For example, a rat LSEC-specific antibody has been reported (Ohmura, T. K. et al. (1993) *Journal of Histochemistry and Cytochemistry* 41:1253–1257, herein incorporated by reference). The characterization of the antigen and subsequent isolation of its promoter employs conventional techniques of molecular biology, chemistry, biochemistry, and recombinant DNA technology, which are within the skill of the art. Such techniques are explained fully in the literature. See for example, Maniatis et al. (1982) *Molecular Cloning: A Laboratory Manual* (Cold Spring Harbor Laboratory Press, Cold Spring Harbor, N.Y.); Glover, ed. (1985) *DNA Cloning, Vols. I and II;* Gait, ed. (1984) *Oligonucleotide Synthesis;* Hames and Higgins, eds. (1984) *Nucleic Acid Hybridization;* and the series *Methods in Enzymology* (Colowick and Kaplan, eds., Academic Press, Inc.).

In certain embodiments, the delivery of the nucleotide sequence encoding factor VIII can be identified in vitro or in vivo by including a marker in the expression cassette. The marker will result in an identifiable change in the genetically transformed cell. Drug selection markers include for example neomycin, puromycin, hygromycin, DHFR, GPT, zeocin and histidinol. Alternatively, enzymes such as herpes simplex virus thymidine kinase (TK) or immunological markers can be used. Further examples of selectable markers are well known in the art.

It is recognized that multiple alterations can be envisioned for the design of the expression cassette used in the methods of the present invention. For instance, the cassette may be designed for the insertion of the nucleotide sequence encoding the factor VIII polypeptide using homologous or site-specific recombination systems (i.e., Cre or FLP recombination systems).

The expression cassette may also contain at least one additional gene to be co-transformed into the host cells. For example, it may be advantageous to coexpress von Willebrand factor with factor VIII in the LSECs. The nucleotide coding region of the von Willebrand factor is known in the art. See, for example, U.S. Pat. No. 5,900,467.

The expression cassette of the present invention may be introduced into LSECs by standard methods of transfection, including, but not limited to, liposome-polybrene-, DEAE dextran-mediated transfection, electroporation, calcium phosphate precipitation, microinjection, or velocity driven microprojectiles ("biolistics"). Such techniques are well known by one skilled in the art. Alternatively, one could use a system that delivers the DNA construct in a gene delivery vehicle. The gene delivery vehicle may be viral or chemical. Various viral gene delivery vehicles can be used with the present invention. In general, viral vectors are composed of viral particles derived from naturally occurring viruses. The naturally occurring virus has been genetically modified to be replication defective and does not generate additional infectious viruses. The viral vector also contains an expression cassette capable of expressing the factor VIII protein.

Many viral vectors are known in the art including, for example, retroviruses, adeno-associated viruses, and adenoviruses. Other viruses useful for gene transfer include, but a not limited to, herpes virus, mumps virus, poliovirus, Sindbis virus, and vaccinia virus, such as, canary pox virus. The methods for producing replication-deficient viral particles and for manipulating the viral genomes are well known. See, for examples, Rosenfeld et al. (1991) *Science* 252:431–434, Rosenfeld et al. (1992) *Cell* 68:143–155, and U.S. Pat. No. 5,882,877 (adenovirus); U.S. Pat. No. 5,139, 941 (adeno-associated virus); U.S. Pat. Nos. 4,861,719, 5,681,746, and Miller et al. (1993) *Methods in Enzymology* 21 7:581 (retrovirus), all of which are herein incorporated by reference. Therefore, given the knowledge in the art, viral vectors can be readily constructed for use in LSEC transformations. In specific embodiments, the LSECs will be transformed with an adeno-associated virus containing an expression cassette capable of expressing the factor VIII protein. Adeno-associated viruses are known to efficiently transform cells and to elicit a less severe immune response than other viral vectors.

The virus may also have additional genetic alterations that deliver the virus to a specific cell type. Cell-targeting may be achieved by the viral expression of a ligand that binds a receptor expressed on liver cells. See for example, U.S. Pat. No. 5,817,789, herein incorporated by reference, and references cited therein. In an embodiment of the present invention, the gene delivery vehicle is targeted to cells expressing the lipoprotein receptor related protein, LRP. LRP is expressed in several vascular cell types, smooth muscle cells, endothelia cells (including LSECs), macrophages, and hepatocytes (Strickland, D. K. et al. (1995) *FASEB J.* 9:890:898, Schmoelzl, S. et al. (1998) *Laboratory Investigation* 78:1405–1413; all of which are herein incorporated by reference).

Lipoprotein lipase (LPL) is a ligand of LRP. A fragment of LPL consisting of amino acid residues 313–448 has been shown to bind to LRP with a high affinity (Chappell, D. A. et al. (1994) *J. Biol. Chem.* 269:18001–18006, herein incorporated by reference). Fusion of this LPL fragment to a viral coat protein will target the virus to cells expressing LRP. In an embodiment of the present invention, a gene delivery vehicle is designed to express a fragment of Lipoprotein Lipase (LPL). This allows delivery of the vector to the liver cells expressing LRP.

The expression cassette containing nucleic acid sequences encoding the factor VIII polypeptide may also be administered to LSECs by a non-viral gene delivery vehicle. Such chemical gene delivery vehicles include, for example, a DNA- or RNA-liposome complex formulation or a naked DNA. See, for example, Wang et al. (1987) *Proc. Natl. Acad. Sci. U.S.A.* 84:7851, U.S. Pat. Nos. 5,844,107, 5,108,921, and Wagner et al. (1991) *Proc. Natl. Acad. Sci. U.S.A.* 88:4255–4259, all of which are herein incorporated by reference. For examples of liver cell targeting using liposome complex formulations see U.S. Pat. No. 5,817,789, herein incorporated by reference. The non-viral gene delivery vehicles can be targeted to specific cell types. See for example, U.S. Pat. Nos. 5,844,107, 5,108,921, Wagner et al. *PNAS* 88:4255–4259. The non-viral gene delivery vehicle can be coupled to LPL. This will allow specific targeting of the gene delivery vehicle to cells expressing LRP.

In embodiments of the invention, LSECs are transformed with a gene delivery vehicle specifically targeted to LRP-expressing cells using the LPL ligand. In addition, an endothelial-specific promoter or an LSEC -specific promoter is used to direct the expression of the nucleic acid sequence encoding the factor VIII protein. This combination allows for the preferential expression of factor VIII in the LSECs and not in the liver hepatocytes.

The present invention provides methods for the expression of a factor VIII polypeptide through both the in vitro and in vivo genetic modification of LSECs. By "isolated" LSEC is intended a primary or secondary LSEC cell. As used herein an "LSEC primary cell" includes cells present in a suspension of cells isolated from a vertebrate source, preferably mammalian (i.e., rat, mouse, pig, or human) (prior to their being plated, i.e., attached to a tissue culture substrate such as a dish or flask), and cell suspensions derived from these plated cells. "LSEC secondary cell" refers to LSEC cells at all subsequent steps in culturing. That is the first time a plated primary cell is removed from the culture substrate and replaced (passaged), it is referred to as a secondary cell, as are all cells in subsequent passages. An "LSEC cell strain" consists of secondary cells which have been passaged one or more times; exhibit a finite number of mean populations doublings in culture; exhibit properties of contact-inhibition, anchorage dependant growth (except for cells propagated in suspension culture); and are not immortalized. An LSEC primary culture or secondary cell culture is substantially free of any other cell types. By substantially free is intended the LSEC culture has less than 30%, 20%, 15%, 10%, 9%, 8%, 7%, 6%, 5%, 4%, 3%, 2% or 1% of a contaminating cell type.

In specific embodiments, the methods of the invention provide for genetic modification of LSECs in vitro. Assays to determine the in vitro transformation efficiency of the LSECs with the nucleotide sequence encoding a factor VIII polypeptide are well known in the art. For example, the levels of the therapeutic mRNA or the levels of factor VIII protein secreted into the culture supernatant may be determined. In addition, the activity of factor VIII in the supernatant can be assayed by methods commonly known. See, for example, Lubin (1994) *J. Biol. Chem.* 269: 8639–8641 and Duffy et al. (1992) *J. Biol. Chem.* 267: 7821–7827; all of which are herein incorporated by reference. Alternatively, selectable markers can be used to assay for a stable transfection event.

In vivo gene delivery of the nucleotide sequence encoding factor VIII to the LSECs can be accomplished by many different delivery methods including intramuscular, subcutaneous, intravenous or interperitoneal injections, or by administration through nasal or pulmonary routes or by direct administration into a particular tissue. See, for example, Rosenfeld et al. (1991), supra, Rosenfeld et al. (1991 a) *Clin. Res.* 39:311A, Jaffe et al. supra, and Berkner, supra. In vivo gene delivery to the LSECs is preferably accomplished through the administration of the gene delivery vehicle via portal vein injection into a mammalian subject, preferably human. LSECs have a high surface to volume ratio and are the first layer of cells encountered by the gene delivery vehicle following its injection into the portal vein. This mode of delivery ensures a high percentage of LSECs will be transformed.

Portal vein injection of the gene delivery vehicle in which an endothelial specific promoter or an LSEC-specific promoter is used to direct the expression of nucleotide sequences encoding factor VIII protein will allow for the preferential expression of factor VIII in the LSECs. In addition, administration via the portal vein of a gene delivery vehicle targeted to cells expressing LRP and expressing the nucleotide sequences encoding factor VIII using an endothelial-specific or LSEC specific promoter will also result in the preferential expression of factor VIII in the LSECs.

For in vivo gene delivery, the number of infectious viral particles and/or the amount of DNA administered will be sufficient to transform a significant population of LSECs. A "significant population" is defined as the number of LSECs that must be transformed to increase the level of factor VIII polypeptide in the plasma and elicit a therapeutic effect.

Ex vivo gene therapy is accomplished by obtaining a biopsy of tissue from the liver, isolating the LSECs from the tissue and establishing a primary culture of the LSECs. Transformation of the isolated LSECs with the DNA construct comprising a nucleotide sequence encoding a factor VIII polypeptide or functional variant thereof, may be accomplished using any of the transfection methods described above, including, for example, a viral gene delivery vehicle or a chemical gene delivery vehicle. The DNA construct comprises an expression cassette that upon introduction into the LSEC cells is capable of expressing the factor VIII protein via a constitutive, an endothelial-specific, or a liver-specific promoter. Alternatively, the expression cassette encoding the factor VIII can be introduced by any other suitable means including calcium phosphate mediated transformation, microinjection, electroporation, osmotic shock and the like. Such methods are known in the art. See, for example, Dubensky et al. (1984) *Proc. Natl. Acad. Sci. U.S.A.* 81:7592, Acsadi et al. (1991) *Nature* 352:815, Wolf et al. (1990) *Science* 247:1465–1468, all of which are herein incorporated by reference.

Following in vitro transformation, the modified LSECs described above may be introduced into a subject, through various standardized routes of administration. Methods of administration are known in the art that result in the genetically transformed LSECs residing in, for example, the liver. For example, the cells may be directly implanted into the subjects liver or can also be injected intravenously or intra-arterially so that they circulate within the individual's bloodstream. Alternatively, the cells can be embedded in a matrix or gel material, such as hybrid matrix implants, or macroencapsulation of LSEC cells in a hydrophilic gel material as described in PCT application WO 95/19430, herein incorporated by reference. Once implanted in the individual, the transfected cells will produce and secrete a factor VIII polypeptide or functional variant thereof in a therapeutically effective amount.

The number of genetically modified LSECs that will be introduced into the subject will vary but will be sufficient to increase the level of factor VIII in the blood and elicit a therapeutic effect. Thus, one skilled in the art will be able to determine the number of genetically modified LSECs that need to be administered. The age, weight, sex, and general physical condition of each subject, as well as the volume of distribution, the half-life and bioavailability of the factor VIII polypeptide, and the in vivo productivity of the genetically modified cells, will be among the primary considerations in determining dosage and route of administration. If necessary, the procedure may be repeated or modified until the desired therapeutic result occurs, for example, relief from the symptoms associated with hemophilia A is achieved.

As described above, the cells used will generally be subject-specific, i.e., obtained from the subject to whom the transfected primary or secondary LSEC cells are to be administered, so that they will not be rejected by the subject's immune system. If, however, this scenario is not possible or desirable, cells may be obtained from another individual, genetically modified as described herein, and implanted into the patient who is suffering from a deficiency in factor VIII.

If the use of cells from a subject other than the recipient is required, administration of an immunosuppressant, alteration of histocompatibility antigens, or use of a barrier device to prevent rejection of the implanted cells can be employed. The barrier device will be made of a material (e.g., a membrane such as XM-50 from Amicon, Beverly, Mass.) that permits the secreted product to pass into the recipient's circulation or tissues, but prevents contact between the implanted cells and the recipient's immune system, and thus prevents an immune response to (and possible rejection of) the cells by the recipient. For further guidance regarding gene therapy, see WO 93/09222, the contents of which are herein incorporated by reference.

The following examples are offered by way of illustration and not by way of limitation.

Experimental

Materials

Gey's balanced salt solution, Hank's balanced salt solution (HBSS), Dulbecco's phosphate-buffered saline (PBS), Liver Digest Medium, DMEM/F-12 medium, and AIM-V medium were purchased from GIBCO-BRL (Gaithersburg, Md.). Penicillin (50 U/ml) and streptomycin (50 $\mu$g/ml) were added to DMEM/F-12 medium. Collagenase (type IV), gelatin, and dibutyryl cAMP were purchased from Sigma Chemicals (St. Louis, Mo.). DNAse I was purchased from Boehringer Mannheim (Indianapolis, Ind.). The following murine monoclonal $IgG_1$ $\kappa$ antibodies were purchased from Pharmigen (San Diego, Calif.): FITC-conjugated anti-PECAM-1 (anti-CD31), FITC-conjugated anti-VCAM-1 (anti-CD106), PE-conjugated anti-ICAM-1 (anti-CD54), the corresponding FITC-conjugated- and PE-conjugated isotype-specific control antibodies, and biotinylated anti-ICAM-1. FITC-conjugated wheat germ agglutinin (WGA) was purchased from Molecular Probes (Eugene, Oreg.). Streptavidin-conjugated and CD11b-conjugated magnetic beads were purchased from Miltenyi, Inc. (Auburn, Calif.).

Liver Cell Isolation

Single cell suspensions were prepared from livers of five or six 10–12 week old Balb/c female mice (Harlan Sprague Dawley Laboratories, Indianapolis, Ind.). Mice were anesthetized intraperitoneally with sodium pentobarbital. Livers were perfused in situ via the portal vein with 15–20 ml Gey's balanced salt solution with drainage through a severed inferior vena cava. Livers were perfused with 60 ml of Liver Digest Medium at a flow rate of 5 ml/min and then removed and submerged in DMEM/F-12 medium on ice.

Subsequent steps were carried at 4° C. unless indicated otherwise. To purify hepatocytes, liver capsules were gently disrupted in DMEM/F-12 medium using two one-milliliter serological pipettes. The hepatocytes were allowed to settle by gravity for 5 min and then washed five times with DMEM/F-12 medium by gravity sedimentation.

To obtain sinusoidal cells (LSECs and Kupffer cells), gall bladders were removed and the livers were minced with a sterile razor blade. The livers were digested with 0.02% (w/v) collagenase and 0.0005% (w/v) DNAse I in 50 ml of HBSS containing 20 mM HEPES, pH 7.4 at 37° C. for 30 min with occasional shaking. The resulting cell suspension was filtered through a 75 $\mu$m nylon mesh and the filtrate was centrifuged at 50×g for 5 min to pellet the hepatocytes. The supernatant was removed and pelleted by centrifugation at 600×g for 10 min. The cells were washed once with HBSS, layered over a 1.037 g/ml solution of Percoll (Pharmacia) and centrifuged at 400×g for 20 min. The resulting upper layer and interface, containing Ito cells, dead cells and debris, were removed. The lower layer was diluted threefold with Dulbecco's PBS and centrifuged at 600×g for 10 min to pellet the cells.

Kupffer cells and LSECs were isolated by CD11b-conjugated and biotinylated ICAM-1/streptavidin-conjugated magnetic bead cell sorting, respectively, over $MS^+$ MiniMACS separation columns (Miltenyi, Inc.) according to instructions supplied by the manufacturer. Briefly, the cell pellet from the Percoll centrifugation step was suspended in 0.45 ml Dulbecco's PBS/0.5% biotin-free bovine serum albumin/2 mM EDTA, followed by addition of CD11b-conjugated magnetic beads and elution of CD11b-positive cells. Biotinylated ICAM-I antibodies (50 $\mu$g/ml) were added to the CD11b-nonadherent fraction for 15 minutes, followed by isolation of LSECs using streptavidin-conjugated magnetic beads. Both preparations were eluted with DMEM/F-12 medium/15% FBS/dibutryl cAMP (250 $\mu$g/ml) and stored at concentration of $1-2\times10^6$ cells per ml. Approximately $3\times10^6$ LSECs were obtained from six livers.

Cell Culture

Cells were cultured at 37° C. in a humidified atmosphere containing 5% $CO_2$. Freshly isolated LSECs were plated onto 0.1% (w/v) gelatin-coated 12-well Falcon 3043 plates (401 $mm^2$ per well) at a density of $1\times10^5$ cells per well. The cells were incubated for two hours, non-adherent cells were washed off with HBSS and fresh medium containing DMEM/F-12/15% FBS/250 $\mu$g/ml dibutyryl cAMP was added. Initially, the cells were 30–40% confluent and grew to confluence in one or two days. Each well contained approximately $1\times10^5$ cells at confluence. Confluent cultures of human umbilical vein endothelial cells and human dermal microvascular endothelial cells were purchased from the Emory Skin Cell Center and were also maintained in DMEM/F-12/15% FBS/250 $\mu$g/ml dibutyryl cAMP. For studies of factor VIII secretion, confluent monolayers were washed three times with HBSS and then maintained in AIM-V, a serum-free cell culture medium for two days.

Freshly isolated hepatocytes were plated onto collagen-coated Costar six-well plates (962 $mm^2$ per well) at $6\times10^5$ cells per well for 30 min in DMEM/F-12/10% FBS. Non-adherent cells were washed off with HBSS. Hepatocytes were maintained in medium containing DMEM/F-12 plus 10% FBS for two days prior to assay for factor VIII secretion.

Characterization of Cells

Purified cells were prepared for differential staining and light microscopy by centrifugation onto microscope slides using a Cytospin 3 Cell Preparation System (Shandon Scientific, Cheshire, England). Cells were stained using a modified Wright-Giemsa stain (Diff-Quik, Baxter, McGaw Park, Ill.).

Freshly isolated LSECs and trypsin/EDTA-solubilized cultured LSECs were characterized further by flow cytometry. Cells were diluted to $1\times10^5$ cells per ml with Dulbecco's PBS/3% FBS and incubated with saturating concentrations of dye-labeled specific antibody, isotype control antibody or wheat germ agglutinin. The cells were washed once and resuspended in Dulbecco's PBS/3% FBS. Data collection and analysis were done using a Becton Dickinson FACSort flow cytometer and CellQuest software.

RT-PCR Reactions

Total RNA from hepatocyte, Kupffer cell and LSEC preparations and from cultured LSECs was isolated using a RNeasy Mini Kit (QIAGEN, Santa Clarita, Calif.). RNA was quantitated spectrophotometrically at 260 nm using an extinction coefficient of 25 ml/mg/cm. Reverse transcriptase (RT) reactions were conducted using a First-Strand cDNA Synthesis Kit (Pharmacia), 0.2 $\mu$g total RNA template and primers specific for factor VIII, von Willebrand factor (vWf) or factor IX (Table 1).

The resulting cDNA fragments were amplified by PCR using Taq DNA polymerase (Promega, Madison, Wis.) and the primers listed in Table 1. Samples were denatured for 2 min at 94° C., followed by 28 cycles of denaturation for 1 min at 94° C., annealing for 2 min at 55° C., and elongation for 2 min at 72° C. Reactions were completed by a final elongation step for 5 min at 72° C. The products were subjected to 1.5% agarose gel electrophoresis and were visualized using ethidium bromide.

Factor VIII mRNA levels in LSECs and hepatocytes were quantitated by a modification of published competitive RT-PCR procedures (Wang A. M., et al. (1989) *Proc. Natl. Acad. Sci. USA* 86:9717–9721; Powell E. E., et al. (1992) *J. Lipid Res.* 33:609–613; Saghizadeh M., et al. (1996) *J. Clin.*

Invest. 97:1111–1116). In this method, a known concentration of factor VIII-specific cRNA is added to the RT reaction, which produces a cDNA that competes for the native factor VIII cDNA during PCR amplification. The point of equivalence, where cRNA-derived and mRNA-derived cDNA products are equal, determines the number of mRNA molecules in the sample.

To initially test the method, two regions of factor VIII were amplified using cRNAs and PCR primers corresponding to the A3 and C2 domains of murine factor VIII. The PCR products contained intron-spanning sequences to avoid potential signals from contaminating genomic DNA. The cRNAs were identical to endogenous factor VIII mRNA except for an internal 50-bp deletion so that the resulting cRNA-derived PCR product could be distinguished from the endogenous factor VIII PCR product electrophoretically.

primers (underlined). The sequence of the cDNA products was verified by dideoxy sequencing. The cRNA was produced by T3 RNA polymerase-catalyzed in vitro transcription off pBluescript using a Ribomax Transcription Kit (Promega) and purified using a RNeasy Mini Kit. The molar concentration of cRNA was calculated from the absorbance at 260 nm and the molecular weight.

The cRNA-dependent inhibition of endogenous factor VIII cDNA synthesis was quantitated by densitometry of ethidium-bromide stained products. Gel photographs were obtained using a Hewlett-Packard 6200C ScanJet scanner and were analyzed using digitization and quantitation software (UN-SCAN-IT, Silk Scientific, Orem, Utah). Plots of the ratio of mRNA-derived and cRNA-derived products as a function of cRNA concentration were linear. The point of equivalence was determined by linear regression analysis.

TABLE 1

Oligonucleotide primers used for RT-PCR[a]

| Gene | Oligonucleotide (5'→3') | Position[b] | SEQ ID NO |
|---|---|---|---|
| RT Primers | | | |
| fVIII A3 | GCCCATGCTGAGAAGATACCATCG | 6189–6212 | SEQ ID NO: 1 |
| fVIII C2 | GTATTGCTGCTGGGCCTCACATCC | 7341–7364 | SEQ ID NO: 2 |
| factor IX | TTTTCCCCAGCCACTGACATAGCCA | 1044–1068 | SEQ ID NO: 3 |
| vWf | GGCAGTTGCAGACCCTCCTTG | 5124–5144 | SEQ ID NO: 4 |
| PCR Primers | | | |
| fVIII A3 sense | GTCCCTACTCCTTCTATTCTAGCC | 5713–5736 | SEQ ID NO: 5 |
| fVIII A3 antisense | GCCCATGCTGAGAAGATACCATCG | 6189–6212 | SEQ ID NO: 6 |
| fVIII C2 sense | CTTCGCATGGAGTTGATGGGCTGT | 6852–6875 | SEQ ID NO: 7 |
| fVIII C2 antisense | TCATCATAGGTGTGGATGAGTCCTG | 7227–7251 | SEQ ID NO: 8 |
| factor IX sense | CTCGAGTTGTTGGTGGAGAAAACG | 668–691 | SEQ ID NO: 9 |
| factor IX antisense | TTTTCCCCAGCCACTGACATAGCCA | 1044–1068 | SEQ ID NO: 10 |
| vWf sense | ATGATGGAGAGGTTACACATC | 4015–4035 | SEQ ID NO: 11 |
| vWf antisense | GGCAGTTGCAGACCCTCCTTG | 5124–5144 | SEQ ID NO: 12 |

[a]Primers were designed based on the murine fVIII (Elder B., et al. (1993) Genomics 16:374–379), murine factor IX (Wu, S. M., et al. (1990) Gene 86:275–278), and murine vWf (Nichols, W. C., et al. (1994) Blood 83:3225–3231) cDNA sequences.
[b]Numbering is based on the cDNA sequences of murine fVIII (GenBank accession number L05573) and murine factor IX (GenBank accession number M23109). vWf numbering is by homology to the human vWf cDNA sequence (Bonthron et al. (1986) Nuc. Acids Res. 14:7125–7127).

This produced 500/450-bp and 400/350-bp products for the A3-specific and C2-specific PCR reactions, respectively.

The first step in the cRNA constructions was synthesis of cDNAs containing 50-bp loop-outs. The cDNAs were synthesized by PCR amplification of RT products obtained from liver total RNA using the A3-specific and C2-specific primers shown in Table 1. The A3 sense loop-out primer, 5'-AAA A CT GCA G GT CCC TAC TCC TTC TAT TCT AGC CGT CAA GCC TAA TGA AAC CAA AAT TTA TTT TTG G-3'(SEQ ID NO: 13), corresponded to murine factor VIII cDNA nucleotides 5713–5819 with the deletion of nucleotides 5737–5786. The A3 antisense primer, 5'-TTT T CT GCA G GC CCA TGC TGA GAA GAT ACC ATC G-3'(SEQ ID NO:14), corresponded to nucleotides 6189–6212. The C2 sense loop-out primer, 5'-AAA A CT GCA G CT TCG CAT GGA GTT GAT GGG CTG TAG ATA CAC AAA TCA CTG CCT CAT CC-3'(SEQ ID NO: 15), corresponded to nucleotides 6852–6950 with the deletion of nucleotides 6876–6925. The C2 downstream primer, 5'-TTT T CT GCA G GT ATT GCT GCT GGG CCT CAC ATC CTA G-3'(SEQ ID NO:16), corresponded to nucleotides 7341–7364.

The loop-out cDNA products were cloned into pBluescript II phagemid (Stratagene, La Jolla, Calif.) using Pst I restriction sites that had been incorporated into the PCR Factor VIII Activity Assay in Endothelial Cell Culture Supernatants The measurement of factor VIII in cell culture supernatants was measured using a plasma-free chromogenic assay that measures the thrombin-activated factor VIII-dependent rate of factor X activation by factor IXa as described previously (Lubin et al. (1994) J. Biol. Chem. 269:8639–8641; Duffy et al. (1992) J. Biol. Chem. 267:7821–7827). The reaction components included limiting activated factor VIII, 0.5 nM porcine factor IXa, 425 nM porcine factor X, and 50 $\mu$M phospholipid. The initial rate of factor Xa formation was measured using the chromogenic substrate Spectrozyme Xa (American Diagnostica, Greenwich, Conn.). The results were compared to a standard curve prepared using human recombinant VIII of known coagulant activity (provided by Hyland-Immuno Division, Baxter Healthcare, Duarte, Calif.).

Results
Isolation of Liver Cell Populations

Hepatocytes were isolated from liver cell suspensions by low speed centrifugation. They were identified as large (20–25 $\mu$m), frequently binucleate cells with basophilic cytoplasm. The preparation was less than 5% contaminated by other cell types. Kupffer cell preparations were obtained using anti-CD11b magnetic bead cell sorting and identified by their relatively large size (10–12 µm), eccentric nuclei and numerous vacuoles. CD11b-positive preparations contained approximately 80% Kupffer cells/monocytes and 20% granulocytes. LSECs were isolated from the CD11b-negative population by anti-ICAM-1 magnetic bead cell sorting. They were identified by their relatively small size (8–10 µm), clear cytoplasm and oval nuclei. LSEC preparations typically were 90% pure and contained Kupffer cells (2%) and red blood cells (8%) as contaminants.

Figure 1B:
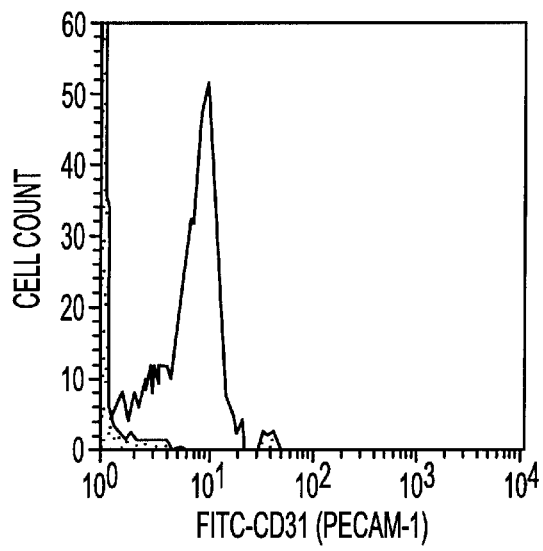
Figure 1C:
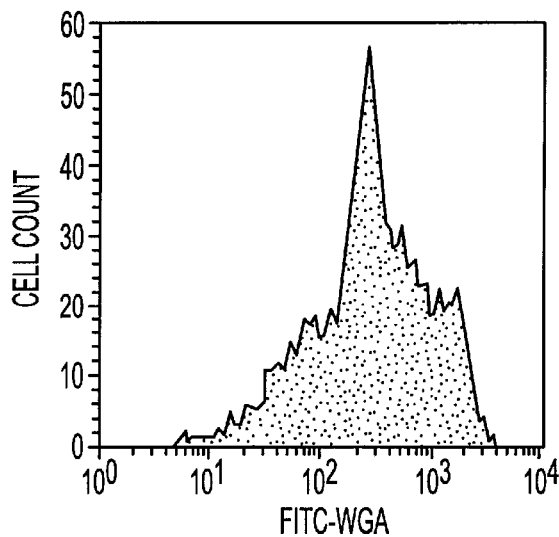

Analysis of the LSEC preparation by flow cytometry demonstrated that the cells expressed cell surface markers ICAM-1 and PECAM-1 and a contained a subpopulation of the cells that bound wheat germ agglutinin (FIG. 1). LSECs did not stain with the monocyte/macrophage specific marker CD14 or the endothelial marker VCAM-1 (data not shown). These findings are similar to previously described phenotypic characteristics of murine LSECs, which were ICAM-$1^+$/PECAM-$1^+$/VCAM-$1^+$ and contained two subpopulations that differentially bound wheat germ agglutinin (Vidal-Vanaclocha et al. (1993) *Hepatology* 18:328–339 and Cardier et al. (1997) *Hepatology* 26:165–175). The reason for the lack of VCAM-1 staining in our LSEC preparation is not known, although the cells became VCAM-$1^+$ after cell culture.

Quantitation of Factor mRNA by Competitive RT-PCR

Initial experiments demonstrated that factor VIII mRNA could be identified by RT-PCR in LSECs and hepatocytes, but not Kupffer cells (data not shown). A quantitative competitive RT-PCR method was developed to measure mRNA levels using a factor VIII-specific cRNA as a source of cDNA competitor as described in *Experimental Procedures*. In this method, the concentration of factor VIII mRNA can be determined by finding the concentration of cRNA that produces equal amounts of mRNA-derived and cRNA-derived PCR (Wang et al. (1989) *Proc. Natl. Acad. Sci. USA* 86:9717–9721).

Separate competitive RT-PCR analysis of total liver was performed on regions corresponding to the A3 and C2 domains of the factor VIII cDNA (Table 1). Levels of $6.5 \times 10^5$ and $7.4 \times 10^5$ factor VIII mRNA transcripts per µg total RNA were obtained using the A3-specific and C2-specific primers, respectively (data not shown). These results were within the experimental error of the method and verified that the region of factor VIII selected for amplification did not bias the measurements. Further experiments were performed using A3-specific primers.

A competitive factor VIII RT-PCR assay of purified LSECs. Quantitation of factor VIII mRNA from purified LSECs was performed. Varying numbers of cRNA molecules and 0.2 µg of total RNA from LSECs were used in competitive RT-PCR reactions followed by agarose gel electrophoresis and ethidium bromide staining. These experiments demonstrated that the concentration of the 500-bp PCR product derived from endogenous factor VIII mRNA is inversely related to the concentration of added competitor cRNA, which produces a 450-bp product (data not shown). Regression analysis of the band intensities yielded a value of $3.3 \times 10^6$ factor VIII mRNA transcripts per µg of total cellular RNA. Similar experiments were done using a hepatocyte preparation. The results of several experiments with LSECs and hepatocytes are shown in Table 2. Purified LSECs contain approximately five-fold more factor VIII transcripts per µg of total cellular RNA than hepatocytes. Because hepatocytes contain more total RNA per cell than LSECs, hepatocytes contain approximately twice as many factor VIII transcripts per cell than LSECs.

In parallel RT-PCR reactions, purified LSECs were positive for vWf mRNA, a marker for endothelial cells and the factor IX mRNA, a hepatocyte marker, was not detected in LSECs (data not shown). Conversely, factor IX mRNA was detected in hepatocytes but vWf mRNA was not (data not shown).

Factor VIII Expression in Cultured LSECs

Primary monolayer cultures of LSECs were established by growing cells on gelatin in the presence of DMEM/F-12/15% FBS/dibutyryl cAMP. LSECs were spindle-shaped and displayed long cytoplasmic extensions prior to confluence (data not shown). As they approached confluence, they formed a polygonal, flat "cobblestone" monolayer (data not shown) that is characteristic of cultured endothelial cells (Jaffe et al. (1973) *J. Clin. Invest.* 52:2745–2756). Cultured LSECs were positive by flow cytometry for ICAM-1, PECAM-1, VCAM-1 and bound wheat germ agglutinin (FIG. 1). Competitive RT-PCR analysis of factor VIII mRNA of cultured LSECs (data not shown) yielded levels that were indistinguishable from purified LSECs (Table 2). Additionally, like purified LSECs, cultured LSECs expressed vWf, but not factor IX (data not shown). Cultured LSECs maintained their phenotypic characteristics when trypsinized, split 1:1 and regrown to confluence. They did not survive a second passage under the growth conditions described in Experimental Procedures.

Figure 2:
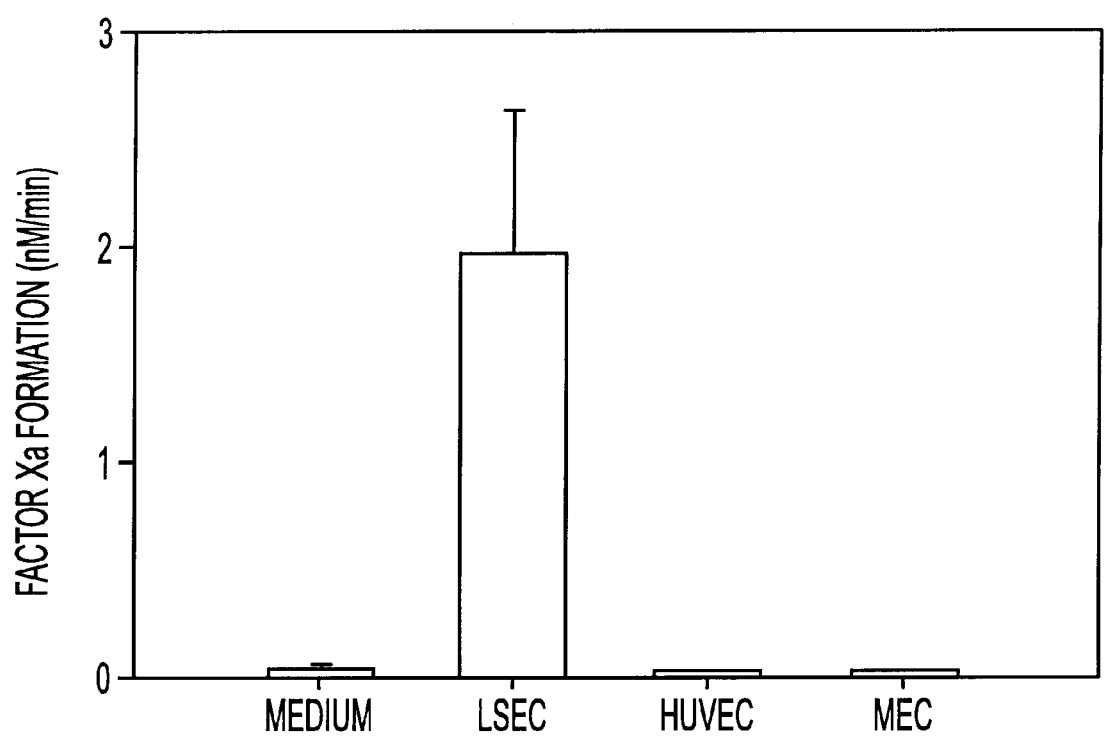
FIG. 2: Secretion of factor VIII from cultured LSECs. Endothelial cell monolayers were incubated in serum-free medium for two days. Supernatants were collected from LSEC, human umbilical vein endothelial cells (HUVEC), or dermal microvascular endothelial cells (MEC) and assayed for factor VIIIa-dependent activation of factor X by factor IXa as described herein. The data represent the mean and standard deviation from cultures obtained from three separate preparations.

The factor VIII-dependent rate of factor Xa formation in LSEC supernatants was significantly greater than medium alone (FIG. 2). The measured rate corresponds to $1.4 \times 10^{-2}$ units per ml of coagulant activity using human factor VIII as a standard. In contrast, rates of factor Xa formation due to human umbilical vein endothelial cells or dermal microvascular endothelial cells were not significantly above background. factor VIII activity was not detected in primary cultures of hepatocytes (data not shown).

TABLE 2

Competitive RT-PCR measurements of FVIII mRNA in LSECs and hepatocytes

| | FVIII mRNA (transcripts/ µg total RNA) | Total RNA (µg/$10^6$ cells) | FVIII mRNA[d] (transcripts/cell) |
|---|---|---|---|
| Purified LSECs | $3.5 \pm 0.3 \times 10^{6a}$ | $10.6 \pm 1.2^a$ | 37 |
| Cultured LSECs | $3.2 \pm 0.5 \times 10^{6b}$ | $10.6 \pm 0.3^b$ | 34 |
| Hepatocytes | $7.5 \pm 0.8 \times 10^{5c}$ | 93 | 70 |

[a] Mean and s.d. from separate determinations from three preparations
[b] Mean and range from separate determinations from two preparations
[c] Mean and range from two RT-PCR reactions from one preparation
[d] Calculated from the values in columns 1 and 2.

Discussion

Hepatic factor VIII gene expression was studied by RT-PCR using purified populations of murine LSECs, hepatocytes, and Kupffer cells. We detected factor VIII mRNA in LSECs and hepatocytes, but not Kupffer cells. The absence of factor IX mRNA, a hepatocyte marker, in purified LSECs excluded the possibility that the factor VIII mRNA was due to contaminating hepatocytes. Conversely, the absence of vWf mRNA, an endothelial cell marker, in the hepatocyte preparation excluded the possibility of a false positive factor VIII signal due to contaminating LSECs.

We also identified factor VIII mRNA in cultured LSECs. This represents the first demonstration of homologous expression of factor VIII mRNA in primary cell culture. In contrast, previous studies of factor VIII expression in cell culture have been conducted by transfecting factor VIII gene fragments into liver cell-derived cell lines (Figueiredo et al. (1995) *J. Biol. Chem.* 270:11828–11838 and Stirling et al. (1998) *Thromb. Haemost.* 79:74–78) or Chinese hamster ovary cells (Kaufman et al. (1988) *J. Biol. Chem.* 263:6352–6362 and Kaufman et al. (1989) *Mol. Cell Biol.* 9:1233–1242). Our results should facilitate studies of factor VIII gene regulation under more physiological conditions.

There has been considerable controversy regarding which type of liver cell synthesizes factor VIII. Factor VIII mRNA was identified in a human hepatocyte preparation by RNAse protection assay (Wion et al. (1985) *Nature* 317:726–729). However, the preparation was contaminated with LSECs and Kupffer cells. In the same study, factor VIII mRNA was not detected in a liver sinusoidal cell preparation. Factor VIII protein was localized by immune electron microscopy to the rough endoplasmic reticulum of both human hepatocytes and LSECs (Zelechowska et al. (1985) *Nature* 317:729–730). In contrast, factor VIII was localized immunohistologically to LSECs but not hepatocytes (Stel et al. (1983) *Nature* 303:530–532; van der Kwast et al. (1986) *Blood* 67:222–227; Kadhom et al. (1988) *Thromb. Haemostas.* 59:289–294; and Shima et al. (1988) *Br. J. Haematol.* 70:63–69). Factor VIII activity was detected in rat LSECs, but not hepatocytes (Hellman et al. (1989) *Br. J. Haematol.* 73:348–355). Factor VIII mRNA levels were not determined in that study.

Our results show that LSECs and hepatocytes make similar amounts of factor VIII mRNA (40 versus 70 transcripts per cell, respectively, Table 2). The ratio of hepatocytes to LSECs in liver is approximately 3 to 1 (Schaffner et al. (1985) *Bockus Gastroenterology*, pp. 2625–2658, W. H. Saunders, Philadelphia and Kuiper et al. (1994) *The Liver: Biology and Pathobiology* pp. 791–818, Raven Press, New York). Thus, the ratio of hepatocyte to LSEC steady-state factor VIII mRNA transcripts in liver is approximately 5 to 1, suggesting that LSECs may contribute 15–20% of the normal hepatic synthesis of factor VIII. Factor VIII levels rise to normal after liver transplantation in patients with hemophilia A, during which there can be no extrahepatic synthesis of factor VIII (Bontempo et al. (1987) *Blood* 69:1721–1724). This indicates that LSECs potentially synthesize hemostatically significant amounts because factor VIII levels in the 15–20% range substantially ameliorate the hemostatic defect in hemophilia A. In fact, factor VIII levels actually are increased in fulminant hepatic failure (Langley et al. (1985) *Thromb. Haemost.* 54:693–696; Fiore et al. (1990) *Hepatology. A Textbook of Liver Disease*, pp. 546–566, Saunders, Philadelphia; and Pereira et al. (1992) *Gut* 33:98–102), which is associated with a profound loss of protein synthesis by hepatocytes. In this setting, levels of all other hepatic coagulation and fibrinolytic factors, including fibrinogen, prothrombin, factors V, VII, IX, X, XI, XII, XIII, prekallikrein, high molecular weight kininogen, protein C, plasminogen, antithrombin III, and a2-antiplasmin are decreased. Up-regulation of factor VIII synthesis by LSECs may occur under these circumstances.

The amount of factor VIII that is secreted by cultured LSECs is consistent with significant synthesis in vivo. There are approximately are $8\times10^{10}$ LSECs in adult human liver. Synthesis of $1.4\times10^{-2}$ units of factor VIII per $10^5$ cells over 48 hours (data not shown) would correspond to total LSEC expression of 5,600 units per day in vivo. By comparison, the estimated daily synthesis of factor VIII in adults is roughly 3000 units because total circulating factor VIII is approximately 3000 units and turnover occurs approximately daily.

In contrast, we did not detect factor VIII activity in cultured hepatocytes. The expected levels are relatively low ($1.4\times10^{-2}$ units per ml observed in LSECs corresponds to 12 pM). Cellular uptake, which occurs during heterologous expression of factor VIII by Chinese hamster ovary cells (Kaufman et al. (1988) *J. Biol. Chem.* 263:6352–6362), or degradation by a protease secreted by hepatocytes, could account for the lack of detectable activity.

The identification of factor VIII in LSECs raises the question of whether endothelial cells from other tissues contribute significantly to factor VIII synthesis. Factor VIII mRNA has been detected in spleen, lymph node, heart, brain, lung, kidney, testes, muscle, and placenta (Wion et al. (1985) *Nature* 31 7:726–729; Lubin et al. (1994) *J. Biol. Chem.* 269: 8639–8641 and Elder et al. (1993) *Genomics* 16:374–3797), which is consistent with a common endothelial cell origin. However, factor VIII has not been identified in cultured endothelial cells from human umbilical vein and other tissues (Wion et al. (1985) *Nature* 317: 726–729 and Jaffe et al. (1973) *J. Clin. Invest.* 52:2757–2764). This is consistent with our finding that human umbilical vein or dermal microvascular endothelium does not contain detectable factor VIII mRNA or activity (FIG. 2). Furthermore, hemophilia A is not cured by kidney transplantation (Webster et al. (1976) *Amer. Jour. Physiol.* 230:1342–1348 and Koene et al. (1977) *Proc. Eur. Dial. Transplant. Assoc.* 14:401–406), which further indicates that significant factor VIII synthesis is not a general property of endothelium. The inability of bone marrow transplantation to cure hemophilia A (Storb et al. (1972) *Blood* 40:234–238) also excludes cells of the monocyte/macrophage system as a source of factor VIII synthesis, which is consistent with our finding that Kupffer cells do not contain detectable factor VIII mRNA.

However, several observations suggest that the extrahepatic synthesis of factor VIII can be clinically significant. The most compelling finding is that liver transplantation from hemophilia A dogs to normal dogs does not produce hemophilia A (Webster et al. (1971) *Amer. Jour. Physiol.* 220:1147–1154). Additionally, spleen transplantation has been reported to produce increased factor VIII levels in human (Storb et al. (1972) *Blood* 40: 234–238; Hathaway et al. (1969) *Transplantation* 7:73–75; Liu et al. (1995) *Arch. Surg.* 130:33–39; and Liu et al. (1994) *Transpl. Int.* 7:201–206) and canine hemophilia A (Norman et al. (1968) *Surgery* 64:1–14), although other investigators have not observed this in the canine system (Marchioro et al. (1969) *Science* 163:188–190 and Webster et al. (1971) *Amer. Jour. of Physiol.* 220:1147–1154). Overall, these findings, combined with the unequivocal demonstration of endothelial synthesis of factor VIII in the present study, are most consistent with the hypothesis that both LSECs and nonhepatic endothelial cells contribute significantly to factor VIII synthesis.

Factor VIII circulates bound noncovalently to vWf. In contrast to factor VIII, vWf has been identified throughout the vascular endothelium and is widely used as an endothelial cell marker. Interestingly, vWf mRNA levels in liver are low relative to other tissues (Yamamoto et al. (1998) *Blood* 92:2791–2801). Circulating factor VIII protein levels are regulated by vWf (Bloom, A. L. (1979) *Clin. Haematol.* 8:53–77 and Lenting et al. (1998) *Blood* 92:3983–3996). Infusion of vWf into patients with severe von Willebrand disease leads to a rapid increase in circulating factor VIII levels (Cornu et al. (1963) *Br. J. Haematol.* 9:189 and Weiss et al. (1977) *J. Clin. Invest.* 60:390–404). This increase occurs without an increase in synthesis of factor VIII mRNA (Kaufman et al. (1999) *Blood* 93:193–197). This indicates that vWf increases secretion of stored factor VIII in this condition. Whether vWf influences factor VIII mRNA and/or protein secretion under normal conditions is unknown. The identification of factor VIII and vWf synthesis in the same cell type raises the possibility of coordinate gene regulation in vivo. The availability of cultured LSECs that synthesize both factor VIII and vWf should facilitate studies in this area.

Hemophilia A is an attractive target for gene therapy. Our finding that the LSEC can support substantial synthesis of factor VIII make it a potentially attractive host for factor VIII synthesis. Portal vein infusion of a suitable vector could deliver factor VIII directly to LSECs. Alternatively, factor VIII could be introduced into cultured LSECs ex vivo, followed by autologous transplantation. Subsequent expression of factor VIII by transduced LSECs under physiological conditions, particularly with respect to regulatory control by vWf, could offer a superior approach to the management of hemophilia A.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for the expression of a polypeptide comprising:
   a) stably introducing into an isolated liver sinusoidal endothelial cell a DNA construct comprising a nucleotide sequence encoding a factor VIII polypeptide or a functional variant thereof; and,
   b) culturing said liver sinusoidal endothelial cell under conditions such that the factor VIII polypeptide or a functional derivative thereof is expressed and secreted from said liver sinusoidal endothelial cell, wherein the culturing of said liver sinusoidal endothelial cell occurs in vitro.

2. The method of claim 1, wherein said DNA construct further comprises a promoter operably linked to the nucleotide sequence encoding factor VIII polypeptide or a functional variant thereof.

3. The method of claim 2, wherein said promoter is an endothelial-specific promoter.

4. The method of claim 2, wherein said promoter is a constitutive promoter.

5. The method of claim 1, wherein said DNA construct is contained in a gene delivery vehicle.

6. The method of claim 5, wherein said gene delivery vehicle is a non-viral vector.

7. The method of claim 1, wherein said DNA construct is introduced into said liver sinusoidal endothelial cell by liposome-mediated transfection, polybrene-mediated transfection, DEAE dextran-mediated transfection, electroporation, calcium phosphate precipitation, microinjection, or velocity driven microprojectiles.

8. An isolated liver sinusoidal endothelial cell having stably incorporated a DNA construct comprising a nucleotide sequence encoding a factor VIII polypeptide or a functional variant thereof, operably linked to a promoter active in said liver sinusoidal endothelial cell.

9. The transformed liver sinusoidal endothelial cell of claim 8, wherein said promoter is endothelial-specific.

10. The transformed liver sinusoidal endothelial cell of claim 8, wherein said promoter is constitutive.

11. The transformed liver sinusoidal endothelial cell of claim 8, wherein said cell is from a mammal.

12. The transformed liver sinusoidal endothelial cell of claim 8, wherein said cell is from a human.

* * * * *

UNITED STATES PATENT AND TRADEMARK OFFICE
CERTIFICATE OF CORRECTION

PATENT NO. : 6,517,830 B1
DATED : February 11, 2003
INVENTOR(S) : Lollar et al.

It is certified that error appears in the above-identified patent and that said Letters Patent is hereby corrected as shown below:

Column 1,
Line 11, insert the following paragraph before "FIELD OF THE INVENTION":
-- FEDERALLY SPONSORED RESEARCH OR DEVELOPMENT
The research underlying this invention was supported in part with funds from National Institute of Health grant no. R01 HL40921. The United States Government may have an interest in the subject matter of this invention. --

Signed and Sealed this

Twenty-first Day of June, 2005

JON W. DUDAS
*Director of the United States Patent and Trademark Office*